United States Patent [19]

Marx

[11] 4,053,420

[45] Oct. 11, 1977

[54] BLOOD FILTER

[75] Inventor: Günter Helmut Marx, Grafelfing, Germany

[73] Assignee: Dr. Eduard Fresenius Chemisch-Pharmazeutische Industrie KG., Bad Homburg, Germany

[21] Appl. No.: 676,539

[22] Filed: Apr. 12, 1976

[30] Foreign Application Priority Data

Apr. 14, 1975 Germany .............................. 2516175

[51] Int. Cl.$^2$ .................... B01D 27/00; B01D 35/00; B01D 35/28

[52] U.S. Cl. ................. 210/435; 128/214 R; 210/483; 210/505; 210/508; 210/DIG. 23

[58] Field of Search ............ 210/491, 496, 503, 505, 210/507, 508, 500, 348, 435, 446, 497.1; 128/214 B, 128/214 C, 214 R; 19/.32

[56] References Cited

U.S. PATENT DOCUMENTS

| | | | |
|---|---|---|---|
| 2,238,977 | 4/1941 | Jackson et al. | 19/.32 |
| 3,069,831 | 12/1962 | Young et al. | 210/496 |
| 3,107,412 | 10/1963 | Hall et al. | 19/.32 |
| 3,334,752 | 8/1967 | Matravers | 210/497.1 |
| 3,356,226 | 12/1967 | Miller et al. | 210/497.1 |
| 3,379,003 | 4/1968 | Kanbar | 19/.32 |
| 3,388,536 | 6/1968 | Nash | 210/496 |
| 3,398,837 | 8/1968 | Adams | 210/497.1 |
| 3,435,608 | 4/1969 | Stanley | 19/.32 |
| 3,448,041 | 6/1969 | Swank | 210/DIG. 23 |
| 3,462,361 | 8/1969 | Greenwalt et al. | 210/DIG. 23 |
| 3,516,241 | 6/1970 | Nakano et al. | 19/.32 |
| 3,527,572 | 9/1970 | Urkiewicz | 210/DIG. 23 |
| 3,593,854 | 7/1971 | Swank | 210/491 |
| 3,624,779 | 11/1971 | Miller et al. | 210/497.1 |
| 3,676,991 | 7/1972 | Fairfield | 19/.32 |
| 3,747,769 | 7/1973 | Brumfield | 210/DIG. 23 |
| 3,765,536 | 10/1973 | Rosenberg | 210/DIG. 23 |
| 3,972,818 | 8/1976 | Bokros | 210/DIG. 23 |

*Primary Examiner*—Frank W. Lutter
*Assistant Examiner*—Frank Sever
*Attorney, Agent, or Firm*—Fleit & Jacobson

[57] ABSTRACT

A blood filter for removing dead blood corpuscles, conglomerations of blood corpuscles and foreign components from the blood comprises dense wadding formed from a plastics monofilament or a bundle of long plastics threads.

5 Claims, No Drawings

BLOOD FILTER

The invention relates to a filter for removing decayed blood corpuscles, aggregates of blood corpuscles and foreign components from the blood, comprising a dense unwoven packing of fibres having substantially the same diameter as the blood corpuscles. DT-AS Nos. 1,928,052 and 2,116,497 as well as U.S. Pat. Nos. 3,448,041 and 3,593,854 disclose known blood filters of this type, which consist of a mass of fibrous material in which the fibres, which should not be less than 100 micron long, are present as an unorientated accumulation which is more or less filtered, as in a fleece or loose felt. Accordingly, the known filter consists of a structure resembling cottonwool and built up from fibres having a relatively short staple fibre length.

A decided disadvantage of the known filter resides in the fact that individual fibres, particularly those having a very short staple fibre length, become separated from the fibre felt and are then carried along together with the filtered blood. Nor can such separated fibres be filtered out by further filters because their diameters correspond to the diameter of the blood corpuscles and they can therefore just as readily pass through in the longitudinal direction. Although the diameter of the individual fibres in the known filter wad is within the diameter range of the blood corpuscles to be filtered, the mesh width of the filter is substantially larger than the diameter of the blood corpuscles. The filter action is occasioned by the fact that the components to be filtered out adhere to the fibre surface, so that the filter only has to ensure that all the components of the blood to be filtered come into close proximity with the filter fibres during their passage through the filter. Any further filter having a narrower mesh width could possibly restrain staple fibres separated from a preceding filter. However, filtration of the blood by filters of narrow width is undesired because this leads to additional mechanical stressing of the blood, by which it becomes damaged.

In the blood vessels of patients who have received blood that has been filtered through known filters, it has been possible by means of electron-microscopic examination to prove the presence of staple fibres released from the filters.

It is therefore an object of the invention to provide a blood filter within a filter housing having an inlet and an outlet, from which fibres that are carried away by the blood cannot be released and which avoids mechanical stressing of the blood as far as is possible.

According to the invention, this object is achieved in a filter of the aforementioned kind in that the packing is formed from a single plastics monofilament. No fibres can separate out from the filter according to the invention because the latter consists of a single thread of long length. This thread can be bought into a structure such that meshes of the desired size are created which filter harmful components out of the blood but do not unduly stress same. The filter effect that is obtained can probably be explained by the fact that healthy blood cells possess a negative surface charge. The walls of the vessels in the human body also possess a negative surface charge, so that the blood corpuscles repel one another and the walls of the vessels repel the blood corpuscles because of their like charge and a conglomeration of blood corpuscles and adhesion of the blood corpuscles to the walls of the vessels are effectively prevented. Healthy red blood corpuscles have a life of about 120 days. This period is reduced if the blood becomes damaged by mechanical or biochemical stresses, such as those that might occur during operations. Conglomerations of decayed blood corpuscles can then give rise to blockages in the constricted blood vessels. For this reason, filtration of the supplied blood is necessary during blood transfusions and operations. The filter effect is probably explained by the fact that dead blood corpuscles which no longer have a negative surface charge become deposited on the fibre structure of the filter which exerts no repelling effect on the dead blood corpuscles or aggregations of dead blood corpuscles because they do not possess a charge. The mesh width of the filter can even be larger than small aggregations of blood corpuscles because the latter are deposited on the filter material not because of their size but because of the absence of their electric potential (Zeta potential), which exerts a certain adhesion effect. Healthy blood corpuscles possess a so-called Zeta potential by reason of which they repel one another so that conglomerations are prevented.

The filter according to the invention is desirably made from a crimped thread because this can be brought to the desired filter structure more readily than a smooth thread. Crimped threads have a 'three-dimensional' structure, so that they are more readily brought together to form a filter of the desired mesh width. In contrast with straight threads, the crimping gives rise to a departure of the threads from a longitudinal direction, so that they can be brought together to form a looser mesh or grid structure. The crimping further ensures that the otherwise stiff straight threads can be bent to a small radius. The crimping of the threads can be brought about by thermal, mechanical or other methods known for textile processing.

Instead of crimping, the threads can also be made with a star-shaped cross-section so that, after they have been conglomerated, a wool-like structure results. Crimping of the star-shaped extruded threads is also advantageous.

Desirably, the monofilament is joined at its ends to form an endless thread so that definitely no fibre components can become separated from the filter according to the invention. The filter according to the invention may also consist of a plurality of endless threads or threads having a long length.

A preferred embodiment of the invention makes provision for the fact that filter layers formed from crimped threads or from the threads with star-shaped cross-section, in which layers the threads have a substantially parallel course, are superposed so that the threads extend in different directions. A filter according to the invention built up in this way is more resistant to changes in volume after wetting than a wad formed from staple fibres and in which the individual fibres are unorientated in the wad structure.

The filter threads according to the invention can be made from polyester or some other plastics that is compatible with blood.

It is of particular advantage for the filters according to the invention to be made from cords consisting of a few very long threads. A single or several such thread bundles can then be knotted or otherwise joined at their ends in the aforementioned manner to form endless cords and then be laid together to form the filters. Even thread breakages or interruptions do not have disadvantageous effects in the filter according to the invention because the remaining thread lengths are so large that the threads will be securely retained in the filter structure.

I claim:

1. A filter for removing decayed blood corpuscles, aggregations of blood corpuscles and foreign components from the blood, comprising a filter housing having an inlet and an outlet, said housing containing a dense packing of fibres having substantially the same diameter as the blood corpuscles, said packing consisting of at least one plastics thread of sufficient length to prevent said at least one plastics thread from being carried away by the blood and from being released from said packing, said at least one plastics thread being crimped and arranged to form a mesh having a mesh width functioning to allow healthy blood cells to pass therethrough, said at least one plastics thread being formed from a material which will repel healthy blood cells, said decayed blood cells and said aggregations of blood corpuscles having no negative electric potential and thereby becoming deposited on said packing.

2. The filter of claim 1 in which said at least one plastics thread has a star-shaped cross-section.

3. The filter of claim 1 in which said at least one plastics thread has its ends joined together to form an endless thread.

4. The filter of claim 1 in which said packing comprises filter layers formed from said at least one plastics thread in which layers having a substantially parallel thread course are superposed so that said at least one plastics thread extends in different directions.

5. The filter of claim 1 in which a plurality of said at least one plastics thread are formed into a cord.

* * * * *